(12) United States Patent
Benzon et al.

(10) Patent No.: US 10,004,579 B2
(45) Date of Patent: Jun. 26, 2018

(54) METHOD OF MANUFACTURING A DENTAL SUPERSTRUCTURE

(71) Applicant: Kulzer GmbH, Hanau (DE)

(72) Inventors: Sture Benzon, Helsingborg (SE); Per Olof Leike, Billdal (SE)

(73) Assignee: Kulzer GmbH, Hanau (DE)

( * ) Notice: Subject to any disclaimer, the term of this patent is extended or adjusted under 35 U.S.C. 154(b) by 525 days.

(21) Appl. No.: 14/284,037

(22) Filed: May 21, 2014

(65) Prior Publication Data

US 2015/0072311 A1    Mar. 12, 2015

Related U.S. Application Data

(63) Continuation of application No. 12/438,683, filed as application No. PCT/SE2007/050565 on Aug. 22, 2007.
(Continued)

(30) Foreign Application Priority Data

Aug. 25, 2006  (SE) ...................................... 0601754

(51) Int. Cl.
    *A61C 8/00*    (2006.01)
    *A61C 13/08*   (2006.01)

(52) U.S. Cl.
    CPC .............. *A61C 13/08* (2013.01); *A61C 8/005* (2013.01); *A61C 8/0048* (2013.01);
    (Continued)

(58) Field of Classification Search
    CPC ..... A61C 13/08; A61C 8/0068; A61C 8/0051; A61C 8/0089; A61C 8/005; A61C 8/0048; Y10T 408/03
    See application file for complete search history.

(56) References Cited

U.S. PATENT DOCUMENTS

| 758,750 A | 5/1904 | Haldeman |
| 4,365,958 A * | 12/1982 | Vlock ...................... A61C 3/02 433/225 |

(Continued)

FOREIGN PATENT DOCUMENTS

| DE | 20 2004 016 896 | 4/2005 |
| EP | 0 419 431 | 3/1991 |

(Continued)

OTHER PUBLICATIONS

Chinese Office Action for CN Application No. 2012103206242 dated Feb. 17, 2015 (7 pages).

(Continued)

*Primary Examiner* — Sarang Afzali
*Assistant Examiner* — Ruth G Hidalgo-Hernande
(74) *Attorney, Agent, or Firm* — Merchant & Gould P.C.

(57) ABSTRACT

A dental superstructure, and a manufacturing method thereof, comprising a screw-channel (1), through which screw-channel a screw member is to be inserted, and a screw member seat (3), for providing support to the head of said screw member during fixation of said dental superstructure to a spacer element or an implant (5), are provided. Said dental superstructure is provided with a central axis of said screw-channel (1) and a central axis of said second mouth (4) that at least partly do not coincide. A manufacturing method thereof, a screw-member, and a screwdriver are also provided.

2 Claims, 6 Drawing Sheets

Related U.S. Application Data

(60) Provisional application No. 60/919,041, filed on Mar. 20, 2007.

(52) U.S. Cl.
CPC .......... *A61C 8/0051* (2013.01); *A61C 8/0068* (2013.01); *A61C 8/0089* (2013.01); *Y10T 29/49567* (2015.01); *Y10T 408/03* (2015.01)

(56) References Cited

U.S. PATENT DOCUMENTS

| | | | |
|---|---|---|---|
| 4,832,601 A | 5/1989 | Linden | |
| 5,015,186 A | 5/1991 | Detsch | |
| 5,052,929 A * | 10/1991 | Seal | A61C 8/005 433/173 |
| 5,069,622 A * | 12/1991 | Rangert | A61C 8/005 433/173 |
| 5,116,225 A | 5/1992 | Riera | |
| 5,180,303 A | 1/1993 | Hornburg et al. | |
| 5,344,318 A | 9/1994 | Wilson et al. | |
| 5,645,427 A * | 7/1997 | Peterson | A61C 8/00 433/165 |
| 5,947,733 A | 9/1999 | Sutter et al. | |
| 5,951,288 A * | 9/1999 | Sawa | A61C 8/0033 433/173 |
| 6,227,859 B1 | 5/2001 | Sutter | |
| 6,283,753 B1 | 9/2001 | Willoughby | |
| 6,319,000 B1 | 11/2001 | Branemark | |
| 6,663,387 B2 | 12/2003 | Riley | |
| 6,663,388 B1 | 12/2003 | Schär et al. | |
| 6,848,908 B2 | 2/2005 | Bjorn et al. | |
| 2005/0115368 A1 | 6/2005 | Prager et al. | |
| 2005/0266380 A1 | 12/2005 | Soler et al. | |
| 2008/0311544 A1 | 12/2008 | Lee | |

FOREIGN PATENT DOCUMENTS

| | | | |
|---|---|---|---|
| EP | 0 580 945 | 2/1994 | |
| EP | 0 987 994 | 12/2005 | |
| GB | 1 201 856 | 8/1970 | |
| JP | 1-151453 | 6/1989 | |
| KR | 2001-0091658 | 10/2001 | |
| KR | 2001 0091658 | 10/2001 | |
| KR | 20010091658 | * 10/2001 | |
| KR | 2006 0012036 | 2/2006 | |
| KR | 20060012036 A * | 2/2006 | |
| SE | 506 850 | 2/1998 | |
| WO | WO 98/47441 | 10/1998 | |
| WO | WO 01/70127 | 9/2001 | |
| WO | WO 2005107988 A1 * | 11/2005 | B23H 1/04 |

OTHER PUBLICATIONS

Balaji. "Textbook of Oral Maxillofacial Surgery: Section IV: Minor Oral Surgical Procedures." *Elsevier India*, 2007 pp. 311-315.

Heasman. "Second Edition: Master Dentistry: vol. 2: Restorative Dentistry, Paediatric Dentistry and Orthodontics." *Churchill Livingston El Sevier*. 2003. pp. 133.

Heliden et al. "The Cresco Bridge and Implant Concept: Presentation of a Technology for Fabrication of Abutment-Free Passively Fitting Superstructures." *The Intnl J. of Periodontics & Restorative Dentistry*. vol. 25, No. 1. 2005. pp. 89-94.

Hellden et al. "The Cresco FPD and Implant Concept: Presentation of a Technology for Fabrication of Abutment-Free, Passively Fitting Superstructures." *International J. of Periodontics & Restorative Dentistry*. vol. 25. Nov. 1, 2005. pp. 2-8.

Malik. "$2^{nd}$ Edition: Textbook of Oral and Maxillofacial Surgery." *Jaypee Brothers Medical Publishers (P) Ltd* 2008. pp. 745-746.

Misch. "Contemporary Implant Dentistry: Third Edition." *Mosby El Sevier*. 2008. pp. 31-32.

Misch. "Dental Implant Prosthetics." *El Sevier Mosby*. 2005. pp. 37-38.

Ortorp et al. "Clinical experiences with laser-welded titanium frameworks supported by implants in the edentulous mandible: a 5-year follow-up study." *Int. J. Prosthodont*. vol. 12. No. 1. 1999. pp. 65-72.

Ortorp et al. "Comparisons of precision f fit between cast and CNC-milled titanium implant frameworks for the dentulous mandible." *Int. J. Prosthodont*. vol. 16. No. 2 2003. pp. 194-200.

Ortorp et al. "Photogrammetry and Conventional Impressions for Recording Implant Positions: A Comparative Laboratory Study." *Clinical Implant Dentistry & Related Research*. vol. 7. I. 1. 2005. pp. 43-50.

Ortorp et al. "Screw Preloads and Measurements of Surface Roughness in Screw Joints: An Invitro Study on Implants Frameworks." *Clinical Implant Dentistry & Related Research*. vol. 7. I.3. 2005. pp. 141-149.

Ortorp. "On titanium frameworks and alternative impression techniques in implant dentistry." *The Sahlgrenska Academy at Goteborg University*. 2005. pp. 1-88.

Ortorp."Clinical Experiences of Computer Numeric Control-Milled Titanium Frameworks Supported by Implants in the Edentulous Jaw: A 5-Year Prospective Study." *Clin. Implant Dentistry R. Res*. vol. 6. No. 4. 2004. pp. 199-209.

Swedish Court Decision considering Sutter in an interlocutory injunction case dated May 5, 2011.

International Search Report for International Application No. PCT/SE2007/050565 dated Jan. 22, 2008 (4 pages).

Office Action for co-pending U.S. Appl. No. 12/438,683, dated Mar. 10, 2017.

* cited by examiner

METHOD OF MANUFACTURING A DENTAL SUPERSTRUCTURE

This application is a Continuation of U.S. Ser. No. 12/438,683, filed 10 Aug. 2010, which is a National Stage Application of PCT/SE2007/050565, filed 22 Aug. 2007, which claims benefit of U.S. Ser. No. 60/919,041, filed 20 Mar. 2007, and Swedish Serial No. 0601754-5, field 25 Aug. 2006 and which applications are incorporated herein by reference. To the extent appropriate, a claim of priority is made to each of the above disclosed applications.

FIELD OF THE INVENTION

This invention pertains in general to the field of a dental superstructure and a manufacturing method of said superstructure. More particularly the invention relates to a superstructure to be connected to an osseointegrated dental implant. A superstructure of this kind is disclosed in SE506850.

BACKGROUND OF THE INVENTION

The goal of a dental implant system is to restore the patient to normal function, comfort, aesthetic, speech and health regardless of the current oral condition. These implant systems are based on the implantation of dental implants, such as dental implants made of biocompatible titanium, through insertion into the patient's jawbone. In this respect, the use of biocompatible titanium started in Sweden as early as 1950, and has since then been further developed and spread world-wide. During the 1980's a number of implant systems entered the world market. Methods are known in the art to attach a dental superstructure to an implant. A couple of methods are based on the use of a screw member. Theses screw members can attach the superstructure to the implant, either directly or via spacers.

When implants are implanted in the mouth of a patient who has been without teeth for some time problems arise due to degeneration of bone. If a person has been without teeth for some time, the jawbone that is not under strain of natural teeth or implants, will dissolve and assimilate over time, yielding less bone material for the proper anchoring of a dental implant. To find enough bone for optimal implantation, the implant has to be angled so that the general axis of the implant projects out of the mouth. Fixing a superstructure with a screw member in a straight screw channel to such implants necessitates that the mouth of the screw channel may be forced to be placed on a visual surface of the dental superstructure. Also, the optimum placement of the implant, due to the present dental situation, often results in a non-optimum placement of the dental superstructure in terms of the patient's aesthetics, phonetics and bite.

Therefore, there is a need in the dental field for greater freedom of placement of a dental implant in order to optimize the stability and success of the implantation, while still achieving good aesthetics, phonetics and bite of the patient.

Furthermore, in the above mentioned dental situation there is a need to be able to use an implant placed optimally with regard to the dental situation, that is, the anatomy of the jawbone, while still allowing the dental superstructure to be applied in an optimal way to said implant, such that the mouth of a screw channel not is visible from outside the mouth of the patient.

The means already known in the art for achieving this goal include the use of angled spacers and dental superstructures attached to the implant with adhesive or with other techniques not based on the use of a screw member. The angled spacers have many drawbacks and are characterized by adding significant height to the superstructure, multiple sources of errors, since the coordination of multiple parts undoubtedly leads this, an unnecessarily high price, as a result of the multiple parts and multiple manufacturing steps, increased risk of bacteriological attack, due to the several corners and surfaces exposable to this, weaker screw for the attachment of the dental bridge, since no follow-up draft of said screw is possible since a structure is applied on top of said angled spacers. It also results in an increased complexity of the attachment of the superstructure to the implant. U.S. Pat. No. 6,848,908 discloses an arrangement including an angled spacer element of this kind, including a first passage and a second passage. The first passage is operative to fasten said spacer element in an implant, and the second passage is operative to fasten a superstructure on said spacer element. Superstructures attached to an implant without using a screw member results in less strength, difficulties in detachment and also incompatibility problems with commercially available implant systems of today.

Furthermore, U.S. Pat. No. 5,947,733 discloses a spacer element with a non-linear bore, connecting a first mouth, intended to be connected to a dental implant, and a second mouth, intended to be connected to a dental superstructure through a screw member engaging with the threaded part (132, 232, 332) of the spacer element. Thus, also this system is in need of spacer elements at least for solving the problem of guiding the mouth of a screw channel, such that it is not visible from outside the mouth of the patient.

There is therefore a need, among others, for a method of attaching or detaching a dental superstructure to a dental implant at a chosen angle without adding additional height to the chosen superstructure.

Thus, there is a need for a new superstructure that may be fastened to an implant without angled spacer elements or superstructures attached to the implant with only adhesive or with other techniques not based on the use of a screw member. There is also need for a simpler, faster and cheaper production method of dental superstructures, while still providing the benefits according to above. Furthermore, there is a need to provide for the possibility of a simple assembly ex situ (outside the patient's mouth) and application in situ (in the patient's mouth).

Hence, an improved superstructure, and a manufacturing method thereof, would be advantageous, and in particular a superstructure, and a manufacturing method thereof, allowing for the exclusion of angled spacer elements or fastening of a superstructure to an implant by adhesives, without being forced to place the mouth of the screw channel on a visual surface of the dental superstructure would be advantageous.

SUMMARY OF THE INVENTION

Accordingly, the present invention seeks to mitigate, alleviate or eliminate one or more of the above-identified deficiencies and to provide an improved superstructure of the kind referred to, and a manufacturing method thereof. For this purpose the superstructure of this kind is characterized in that a central axis of at least one part of a screw-channel and a central axis of a mouth of a screw member seat do not coincide, and the manufacturing method is characterized by drilling a first bore from a first point of said superstructure, which first point is intended to face an implant or spacer element, drilling a second bore from a second point on said superstructure, which second point is intended to provide a mouth of a screw channel for attaching said superstructure to said spacer element or implant.

Advantageous features of the invention are defined in the dependent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DESCRIPTION OF EMBODIMENTS

The following description focuses on embodiments of the present invention applicable to a superstructure, and also to a method of manufacturing said superstructure.

Figure 1:
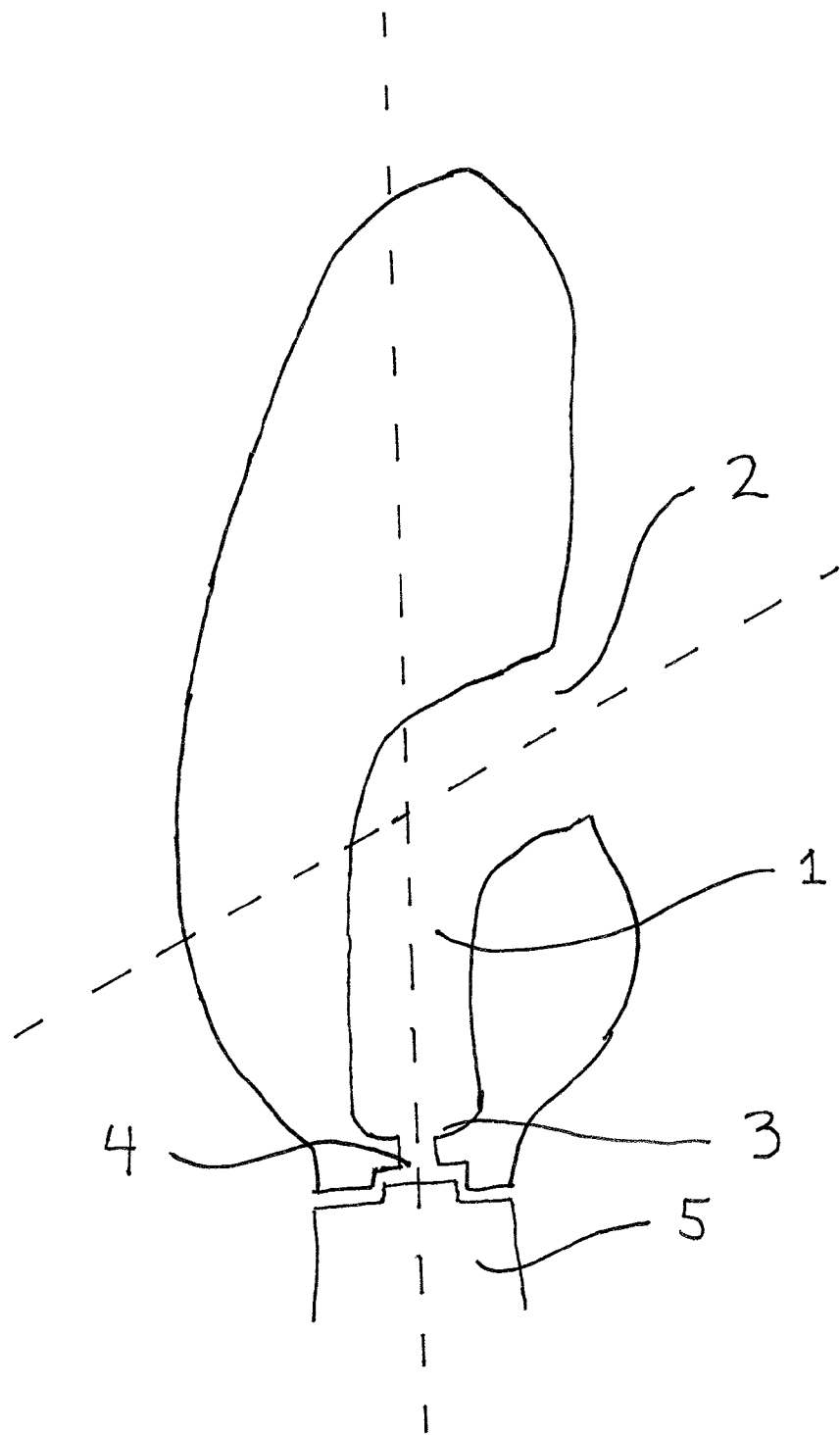
FIG. 1 illustrates a cross-section of an embodiment of a superstructure according to the present invention.

The present invention discloses, according to FIG. 1, a superstructure, and a manufacturing method thereof, comprising a main body, comprising a screw-channel 1 with a first mouth 2, through which screw-channel 1 a screw member is to be inserted, and a screw member seat 3 with a second mouth 4, for providing support to the head of said screw member during fixation of said dental superstructure to a spacer element or an implant 5 through said second mouth 4, whereby a communication is obtained between said first and second mouth, wherein at least one part of a central axis of said screw-channel 1 differs from a central axis of said second mouth 4. In this way the mouth 2 of the screw channel 1 may be located such that the superstructure may be attached/detached to a dental implant or a spacer element 5 where the mouth 2 of the screw channel 1 not is visible from outside the patients mouth.

In one embodiment of the manufacturing method of said superstructure, a superstructure is first manufactured in a way known to the skilled artisan, and then provided with a communication according to above. Such a method is for example disclosed in the Swedish patent SE 509,437, but other manufacturing methods known to the skilled artisan, such as moulding etc., are also within the scope of the present invention.

In one embodiment of the present invention the superstructure is, in contrast to the manufacturing methods according to the prior art, manufactured with integrated spacer elements, milled from one single-piece blank, such that the dental superstructure obtains a main body and spacer elements, wherein said main body and said spacer elements are integrated. In this context the term integrated means that the dental superstructure, comprising a main body, and the spacer elements are consisting of one piece of material, such that no interface is present in between said superstructure and said spacer elements. In this superstructure the dimensions of spacer elements can be varied in accordance with the specific dental situation of a patient intended to receive said replacement structure. When the superstructure is applied the spacer elements will be cooperating with dental implants, inserted and osseointegrated in bone tissue. To obtain a perfect fit, i.e. no gap, between the superstructure and the gum tissue, the length and angle, in respect of the jawbone, superstructure, and jawbone, of the spacer elements will be individual for each spacer in respective spacer position.

In one embodiment the material of said superstructure may be selected from the group comprising titanium, zirconium oxide, alloys of titanium and zirconium, and other biocompatible materials, or combinations thereof.

Figure 2:
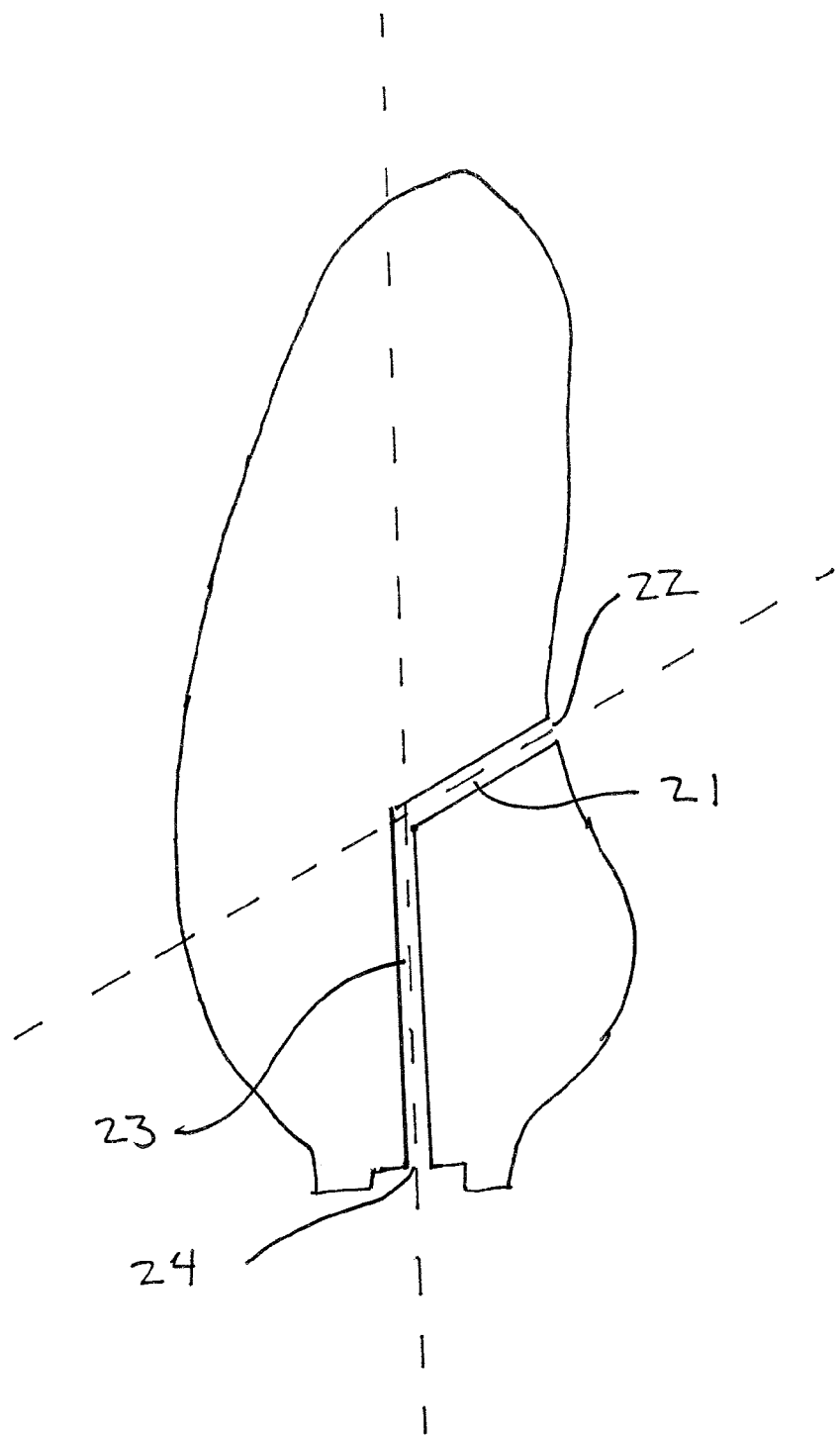
FIG. 2 illustrates a cross-section of a first embodiment of a superstructure according to the principles of the present invention.
Figure 3:
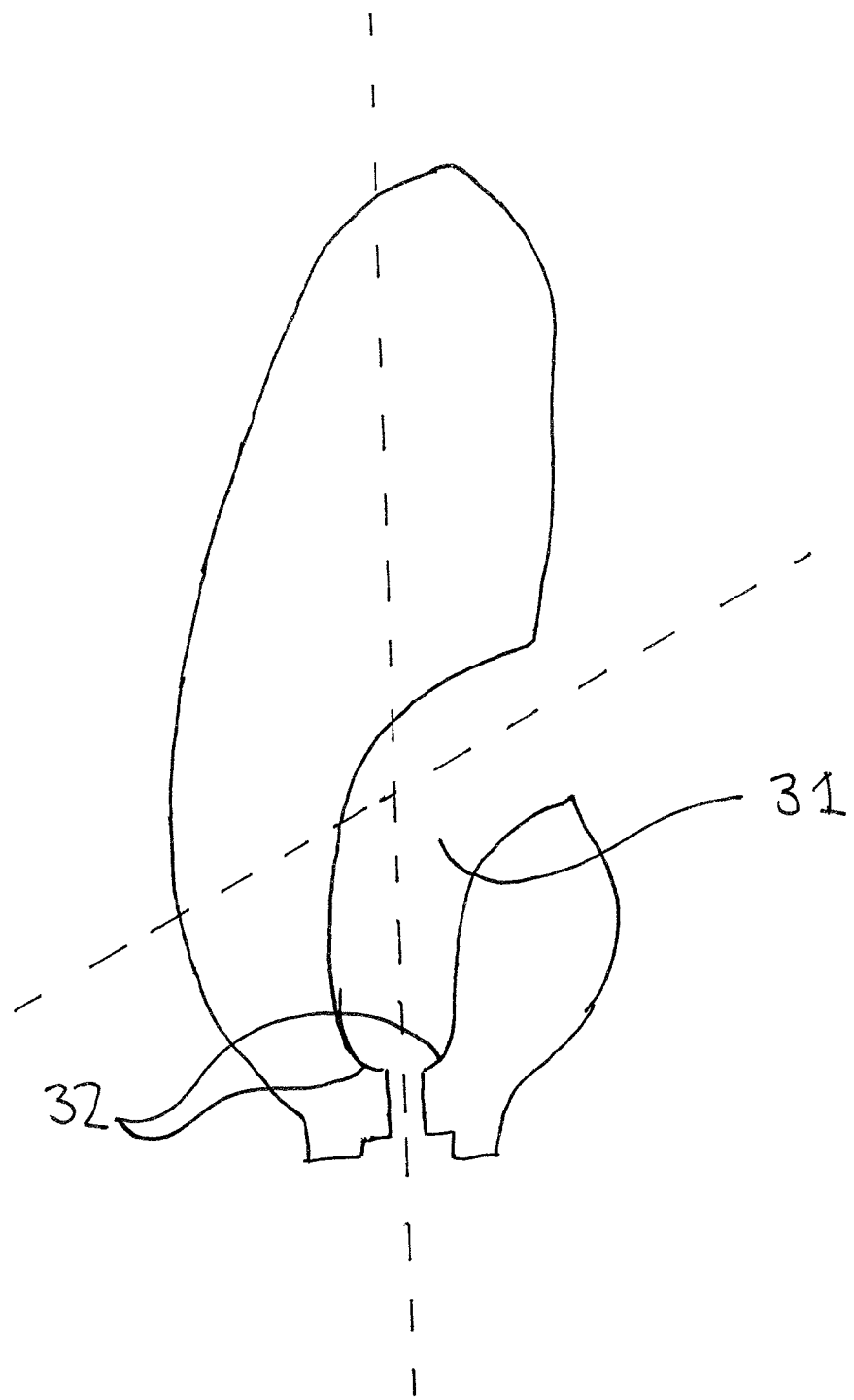
FIG. 3 illustrates a cross-section of a second embodiment of a superstructure according to the principles of the present invention.

When a superstructure, according to any of the embodiments above, has been obtained, a superstructure wherein a central axis of at least one part of a screw-channel differs from a central axis of a mouth of a screw member seat is provided. In one embodiment this is obtained, according to FIG. 2, by drilling a first straight bore 21 from a first point 22 on a side of the dental superstructure, at which first point 22 the mouth of the screw-channel is to be placed, and a second straight bore 23 from a second point 24 on the side of the dental superstructure intended to face the implant or spacer element. It is of course possible to drill the second bore 23 before the drilling of the first bore 21, while still being inside the scope of the present invention. The first and second bores are drilled such that they intersect in the interior of the dental superstructure. Then a third bore 31 may be drilled, according to FIG. 3, after the drilling of said first bore 21 and said second bore 23. This third bore may result in a screw-channel. This third bore may be drilled using said first and second bores as guides. Said third bore may be drilled by using a drill bit with a cutting surface of a sufficient diameter to create a bore through which a screw member may be passed in order to attach the dental superstructure to a spacer element or an implant 5. The third bore 31, i.e. the screw-channel 1, may preferably be drilled close to said second point 24, but not the whole way through. Since the diameter of the third bore 31 is larger than the diameter of said second bore 23, shoulders 32 will form in the screw-channel 1. Said shoulders may then form the seat 3 for a screw member head in the bottom of the screw-channel 1, while being integrated with said superstructure. Thus, a threaded part of a screw member inserted in the screw-channel may be passed through said bore, i.e. said second bore 23, to subsequently attach the dental superstructure to a spacer element or implant 5. Preferably, the diameter of said second bore 23 corresponds to the diameter of the threaded part of the screw member, whereby the screw member may be passed through said bore to fixate the superstructure to an implant or a spacer element 5. Thus, a dental superstructure comprising a main body, comprising a screw-channel 1 with a first mouth 2, through which screw-channel 1 a screw member is to be inserted, and a screw member seat 3 with a second mouth 4, for providing support to the head of said screw member during fixation of said dental superstructure to a spacer element or an implant 5 through said second mouth 4, may be obtained. Hereby a communication is obtained between said first mouth 2 and said second mouth 4. By providing a central axis of at least a part of said screw-channel 1 and a central axis of said second mouth 4 that do not coincide, one may guide the position of said first mouth 2, i.e. through which a screw member is to be inserted, into a position that optimizes the arrangement of the superstructure. This may for example be to locate said first mouth 2 in an aesthetically pleasing position, such as on a surface of the superstructure that can not be seen from outside the mouth of the patient. It is also possible that only the direction of the central axis of a part of the screw-channel 1 differs from the direction of the central axis of the mouth 4 of the screw member seat 3, in accordance with FIG. 1, while still being inside the scope of the present invention.

In one embodiment of the present invention the central axis of said first mouth 2 and the central axis of said second mouth 4 do not coincide.

In one embodiment the first bore 21 and the second bore 23 are made with a conventional twist drill. In this way the first bore 21 and the second bore 23 are drilled to a diameter of a suitable size for passing of the threaded part of a screw member, which screw member is used for attaching the superstructure to a spacer element or implant 5. It is also possible to drill said second bore 23 using a drill bit with a cutting surface of a sufficient diameter to create a bore through which a screw member may be passed in order to attach the dental superstructure to a spacer element or an implant.

Figure 4:
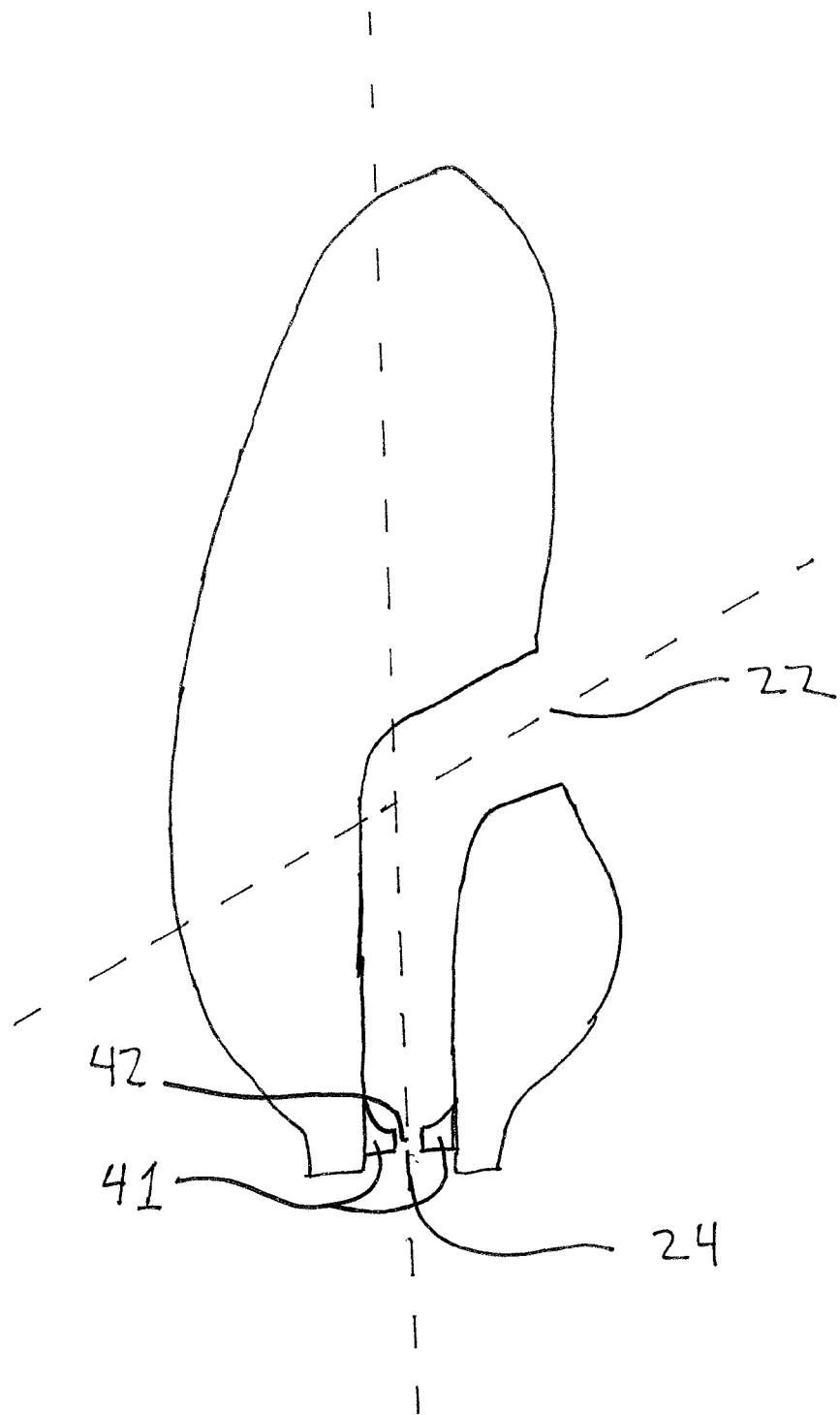
FIG. 4 illustrates a cross-section of a third embodiment of a superstructure according to the principles of the present invention.
Figure 5A:
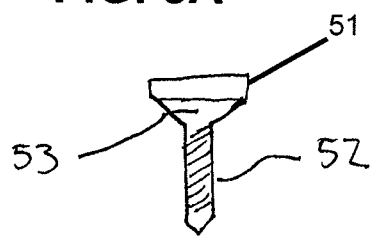
FIG. 5A illustrates a side view of a first embodiment of a screw member according to the principles of the present invention.
Figure 5B:
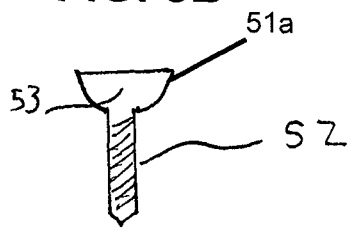
FIG. 5B illustrates a side view of a second embodiment of a screw member according to the principles of the present invention.
Figure 5C:
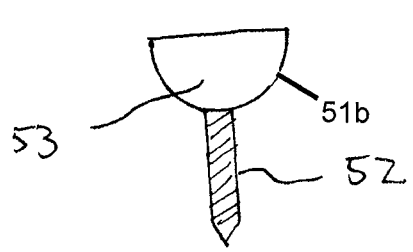
FIG. 5C illustrates a side view of a third embodiment of a screw member according to the principles of the present invention.
Figure 5D:
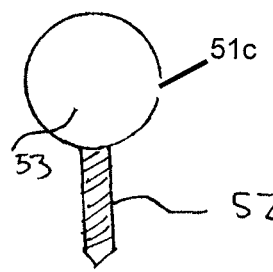
FIG. 5D illustrates a side view of a fourth embodiment of a screw member according to the principles of the present invention.
Figure 5E:
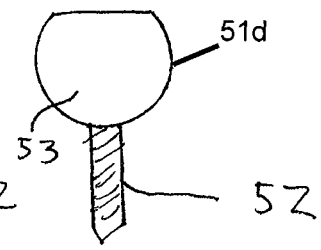
FIG. 5E illustrates a side view of a fifth embodiment of a screw member according to the principles of the present invention.

It is also possible to drill said third bore all the way through said first bore, in accordance with FIG. 4. Then a separate seat 41 for the screw member head may subsequently be inserted and attached to said superstructure. This may be done by attachment techniques known in the art, such as welding or attachment by known adhesive agents. It is even possible to only drill one bore, with a diameter through which a screw member may be passed in order to attach the dental superstructure to a spacer element or an implant. This bore may extend all the way from said first point 22 to said second point 24, or it may extend to a close proximity to said second point 24. If said one bore extends all the way from said first point 22 to said second point 24, a separate seat 41, comprising a hole 42 for matching the threaded part of a suitable screw member, for the screw member head may subsequently be inserted and attached to said superstructure by attachment techniques known in the art, such as welding or attachment by known adhesive agents. If said one bore do not extend all the way from said first point 22 to said second point 24, a bore, matching the threaded part of the screw member, may be drilled from said first point 24, i.e. the point intended to face the dental implant or a spacer element 5, whereby the screw member seat 3 and the second mouth 4 are created, according to the teachings above. By providing a central axis of at least a part of said one bore and a central axis of said bore, matching the threaded part of the screw-member, or said hole, for matching the threaded part of a suitable screw-member, that do not coincide, one may guide the position of a mouth of said one bore, i.e. through which a screw member is to be inserted, into a position that optimizes the arrangement of the superstructure.

An example of a separate seat 41 may be a ring with an outer diameter corresponding to the inner diameter of the screw-channel 1 of the superstructure, and an inner diameter corresponding to the threaded part of the screw member, intended to be used when fixating the superstructure to a spacer element or an implant 5.

In yet another embodiment of the present invention the superstructure is provided with a dental implant seat or a spacer element seat, such as a recess suitable for receiving a protrusion on said dental implant or spacer element. It is of course also possible to provide the superstructure with a protrusion and the dental implant or spacer element with a recess, as long as the seating effect is obtained. This dental implant seat or a spacer element seat provides the advantage of easier assembling of the superstructure on a dental implant or a spacer element.

In one embodiment of the present invention the drill bit used, with a cutting surface of a sufficient diameter to create a bore through which a screw member may be passed, i.e. a screw-channel, such as the drill bit used when drilling said third bore, may have a declining cutting surface, such as an arched, semi-spherical, or spherical cutting surface. In this way the bottom part of the screw-channel may have a declining shape, such as an arched or semi-spherical. Thus, the bottom part may fit with a screw member, according to FIGS. 5A-5E, with a bevelled screw member head 51, arched screw member head 51a, a half-spherical screw member head 51b, spherical screw member head 51c or semi-spherical screw member head 51d and a threaded part 52. Hereby, the diameter of the beveled screw member head 51 may decline, in an arched way, along with a surface 53 intended to, in use, bear upon the shoulders of a screw member seat, from the diameter of the beveled screw member head 51 to approximately a diameter of a threaded part 52 of the screw member. A screw member with a beveled, such as arched, spherical or semi-spherical head may also follow a screw-channel 1 according to the invention. The arched, spherical, or semi-spherical screw member heads 51a, 51c, 51d of the screw member may in this way act as a guide for guiding the screw member from the mouth 2 of screw-channel, i.e. said first point 22, to a seat 3 in the bottom of said screw-channel 1. This seat also comprises said second bore 23, through which the threaded part of the screw member may be passed to attach said superstructure to a spacer element or implant 5. The screw member with a spherical screw member head 51c or semi-spherical screw member head 51d also provides a higher fixing strength and self-centering properties. Since the surface 53 bearing on the shoulders of the screw member seat 3 is arched, such as spherical or semi-spherical, a greater contact surface between the screw member and the shoulders 32 of the screw member seat 3 is obtained. Thereby, the fixating strength obtained from the fixation of the superstructure to the dental implant 5 may be greater than if the surface bearing on the shoulders of the screw member not was arched. The screw member is provided with a recess for receiving a driving means, such as a screwdriver. This recess may be a score, or a slit. The recess may also have other shapes, corresponding to a screwdriver, such as a starshape or a recess with a number of sides, such as tri-tetra-, penta-, or hexagonal. It is of course within the present invention to provide such a recess in any other shapes corresponding to a matching male part on a screwdriver or other driving means. Thus, a screw-member, comprising a threaded part and a screw-head with a recess for receiving a driving means, such as a screwdriver, said screw-head comprising a surface bearing, in use, on shoulders of a screw-member seat, wherein said surface is bevelled towards the threaded part, has been described.

It is also within the present invention to drill said third bore with drilled bits having cutting surfaces with other declining and/or bevelled shapes, such as cone shaped.

Figure 6A:
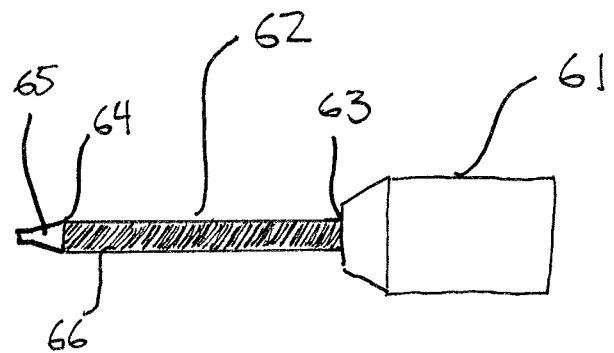
FIG. 6A illustrates a cross-section of a screw driver according to the principles of the present invention.
Figure 6B:
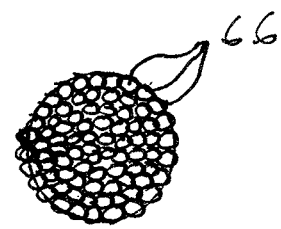
FIG. 6B illustrates a partial enlarged view of a portion of the screw driver of FIG. 6A.

The screw member may be fixed with a screwdriver, in accordance with FIG. 6a, comprising a rotatable handle portion 61 and a flexible and/or bendable shaft portion 62, with a distal end 63 coupled to said handle portion 61 and a proximal end 64 coupled to a tip 65 for driving said screw member with rotation transmitted from said rotatable handle portion 61. Such a screwdriver, for fastening screw members in a screw-channel described above, may comprise a flexible and/or bendable shaft 62. This flexible shaft 62 may in one embodiment comprise twinned wires 66, giving a high torque capacity, independent of shaft bending and angle to the screw member. Said flexible shaft portion 62 may comprise a plurality of wires 66, said wires being twinned in a plurality of layers, in accordance with FIG. 6b, such that said flexible shaft 62 is formed between said distal end 63 and said proximal end 64. The plurality of layers may be twinned such that one part of the layers is twinned in one direction while the other part of the layers is twinned in the other direction. Since said screwdriver has twinned layers of wires, in accordance with FIG. 6b, in two directions the screwdriver is provided with torque capacity in both rotational directions of said flexible shaft. In one embodiment the number of twinned layers may be uneven, whereby the uneven number of layers are twinned in a direction giving the screwdriver a unfastening torque capacity while the even number of layers are twinned in a direction giving the screwdriver a fastening torque capacity. The number of layers may for example be selected within the interval of 2 to 30, such as 10 to 20, but this interval is only intended to be interpreted as guidance and not as limiting. Of course, it is possible to construct screwdrivers with a number of twinned layers outside the given interval, which still may obtain the intended effect. The torque capacity of such a screwdriver may be at least 30 to 35 Ncm.

Figure 6C:
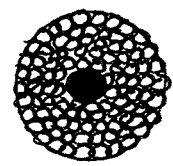
FIG. 6C illustrates a partial enlarged view of a portion of an alternative embodiment of a screw driver according to the principles of the present invention.

In one embodiment the screwdriver is provided with a flexible and/or bendable core, in accordance with FIG. 6c, in said shaft, onto which the plurality of wires are twinned. This flexible and/or bendable core may for example be manufactured of an ordinary plastics or rubber, fulfilling the desired features according to flexing and/or bending in respect of being able to flexate or bend in the screw channel.

In one embodiment the rotatable handle portion 61 and a flexible and/or bendable shaft portion 62 of the screwdriver are separable. In this embodiment the flexible and/or bendable shaft portion 62 may first be inserted in the screw-channel 1, and thereafter the rotatable handle portion 61 is mounted and fixed to said flexible and/or bendable shaft portion 62. Thereby, it may be easier to access the screw member in the screw-channel 1, if the central axis of the screw-channel and the central axis of the second mouth differs in a high degree.

The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described above with reference to specific illustrative embodiments, it is not intended to be limited to the specific form set forth herein. Rather, the invention is limited only by the accompanying claims and other embodiments than the specific above are equally possible within the scope of these appended claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A method of manufacturing a dental superstructure comprising a screw-channel with a first mouth, a screw member seat with a second mouth, wherein the screw member seat provides support to a head of a screw member when the screw member extends through the second mouth to fix said dental superstructure to a spacer element or an implant, wherein a communication is provided between said first mouth and said second mouth, the method comprising:

drilling said communication to form at least one central axis of said screw-channel and a central axis of said second mouth, wherein the at least one central axis of said screw-channel and the central axis of said second mouth do not coincide, wherein said drilling comprises drilling a first straight bore from a first point, and drilling a second straight bore from a second point, such that said first bore and said second bore intersect in an interior of said superstructure to form said communication, and wherein said drilling comprises drilling a third bore using said first bore and said second bore as guides, said third bore drilled using a drill bit with a cutting surface of a sufficient diameter to create said screw-channel through which said screw member is passed in order to attach said dental superstructure to said spacer element or said implant.

2. The method according to claim 1, wherein the drilling of said first bore and the drilling of said second bore comprises drilling with a twist drill providing a diameter sufficient for receiving a threaded part of said screw member.

* * * * *